United States Patent
Mason et al.

(10) Patent No.: US 11,291,762 B2
(45) Date of Patent: Apr. 5, 2022

(54) MICRODROP DRIP CHAMBER

(71) Applicant: CareFusion 303, Inc., San Diego, CA (US)

(72) Inventors: Eugene Mason, La Habra Heights, CA (US); George Mansour, Diamond Bar, CA (US); Jake Smith, Yorba Linda, CA (US)

(73) Assignee: CAREFUSION 303, INC., San Diego, CA (US)

( * ) Notice: Subject to any disclaimer, the term of this patent is extended or adjusted under 35 U.S.C. 154(b) by 62 days.

(21) Appl. No.: 16/160,947

(22) Filed: Oct. 15, 2018

(65) Prior Publication Data

US 2020/0114066 A1    Apr. 16, 2020

(51) Int. Cl.
*A61M 5/14* (2006.01)
*A61M 5/155* (2006.01)
*A61M 39/28* (2006.01)

(52) U.S. Cl.
CPC .......... *A61M 5/1411* (2013.01); *A61M 5/155* (2013.01); *A61M 39/28* (2013.01); *A61M 2205/0294* (2013.01); *A61M 2205/3334* (2013.01); *A61M 2205/3375* (2013.01)

(58) Field of Classification Search
CPC .............. A61M 5/1411; A61M 5/1689; A61M 2205/0294; A61M 2205/3334; A61M 2205/3375
See application file for complete search history.

(56) References Cited

U.S. PATENT DOCUMENTS

| | | | | |
|---|---|---|---|---|
| 3,999,542 A | * | 12/1976 | Shaw | A61M 5/16845 604/507 |
| 4,583,975 A | * | 4/1986 | Pekkarinen | A61M 5/1689 128/DIG. 13 |
| 4,775,368 A | | 10/1988 | Iwatschenko | |
| 4,842,588 A | | 6/1989 | Jones | |
| 5,098,408 A | * | 3/1992 | Tarzian | A61M 5/16881 251/125 |
| 5,575,779 A | * | 11/1996 | Barry | A61M 5/1411 604/122 |

(Continued)

FOREIGN PATENT DOCUMENTS

EP    0018817 A1    11/1980

OTHER PUBLICATIONS

Invitation to Pay Additional Fees and Partial International Search Report for Application No. PCT/US2019/049794, dated Nov. 7, 2019, 13 pages.

(Continued)

*Primary Examiner* — Nathan R Price
*Assistant Examiner* — Melissa A Snyder
(74) *Attorney, Agent, or Firm* — Morgan, Lewis & Bockius LLP (57) ABSTRACT

A disclosed drip chamber for an intravenous (IV) therapy system includes a container configured to hold an IV fluid, a drop former suspended over the container, and an inlet port disposed above the drop former and configured to receive the IV fluid from a reservoir. The drop former has an upper end, a lower tip, and an outer surface extending between the upper end and the lower tip. The inlet port is coupled to the outer surface to permit the IV fluid to descend down the outer surface.

18 Claims, 6 Drawing Sheets

(56) References Cited

U.S. PATENT DOCUMENTS

| | | | |
|---|---|---|---|
| 5,899,665 A * | 5/1999 | Makino | G01F 1/661 |
| | | | 417/20 |
| 6,206,860 B1 | 3/2001 | Richmond | |
| 8,037,657 B2 * | 10/2011 | Sjoberg | E04F 15/02011 |
| | | | 52/592.1 |
| 8,038,657 B2 * | 10/2011 | Davis | A61M 5/1689 |
| | | | 604/253 |
| 2005/0273062 A1 * | 12/2005 | Franksson | A61M 5/1411 |
| | | | 604/254 |
| 2012/0283630 A1 * | 11/2012 | Lee | A61M 5/16827 |
| | | | 604/65 |
| 2016/0287785 A1 * | 10/2016 | Isaacson | A61M 5/16881 |
| 2018/0214642 A1 * | 8/2018 | Deck | A61M 5/1452 |

OTHER PUBLICATIONS

International Search Report and Written Opinion for Application No. PCT/US2019/049794, dated Jan. 3, 2020, 20 pages.

Written Opinion of the International Preliminary Examining Authority for Application No. PCT/US2019/049794, dated Nov. 30, 2020, 10 pages.

International Preliminary Report on Patentability from the International Preliminary Examining Authority for Application No. PCT/US2019/049794, dated May 3, 2021, 20 pages.

* cited by examiner

MICRODROP DRIP CHAMBER

TECHNICAL FIELD

Disclosed embodiments are related to, for example, drip chambers for intravenous (IV) therapy.

BACKGROUND OF THE DISCLOSURE

Medical treatment often involves the use of IV therapy, where fluids such as saline, blood, and/or medication are administered directly into the vein of a patient. IV systems used for IV therapy commonly employ a drip chamber, which allows a clinician (e.g., a nurse) to determine rate at which the IV fluid is administered by manually counting the number of drops over a given period of time. Drip chambers are sometimes classified as macro-drop or micro-drop based on their drop factor, defined as the number of drops per milliliter (mL) of IV fluid provided. For example, macro-drop drip chambers commonly employ a drip factor of about 20 gtts/mL (or drops/mL), while micro-drop drip chambers commonly employ a drip factor of about 60 gtts/mL.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

A drip chamber in an intravenous therapy system may be constrained in the precision at which flow rate can be measured based on its drop factor, in turn constraining the range of flow rates that can be accurately delivered to the patient. For example, neonatal, diabetic, or other fluid restricted patients may require infusion or IV fluid delivery at a slow rate on the order of one mL or a few mL per hour. Even for a micro-drop drip chamber having a drip factor of 60 drops/mL, this can lead to a drop rate as slow as one drop per minute, which may not permit accurate or practical measurement by a clinician using a stopwatch and counting the number of drops. Further, with such low flow rates, even small errors can significantly affect treatment. Automated pumps can provide more precise control over the flow rate, but these add cost and complexity, and pumps may be impractical for certain markets and environments.

In some embodiments disclosed herein, drip chambers, and IV therapy systems and methods employing drip chambers, can allow for smaller drop sizes to permit more accurate metering of low flow rates and/or facilitate more precise flow rate measurements compared to existing technologies. In some embodiments, a drip chamber can employ a solid pin, wire, or other drop former structure that permits IV fluid to wick down an outside surface of the drop former. The drop former can terminate in a sharp solid point to reduce surface area and induce drops to fall from the drop former at a smaller volume. Additionally or alternatively, electronics, such as an ultrasonic or other acoustic energizer, can be employed to stimulate a formation or release of drops from the drop former. Additionally or alternatively, a gas inlet port can be included to permit or other gas to be injected in the drip chamber to break up flow and induce drop release from the drop former. Additionally or alternatively, a piezoelectric sensor can be utilized to detect the impact of falling drops and permit small drops to fall at a faster rate than may be reliably counted with a human eye.

These and other embodiments are discussed below with reference to FIGS. 1-9. However, those skilled in the art will appreciate various alterations and other embodiments that can employ principles of this disclosure without departing from the scope and spirit of the concepts disclosed herein. Thus, it is understood that the detailed figures and discussion provided herein is for explanatory purposes only and should not be construed as limiting.

Figure 1:
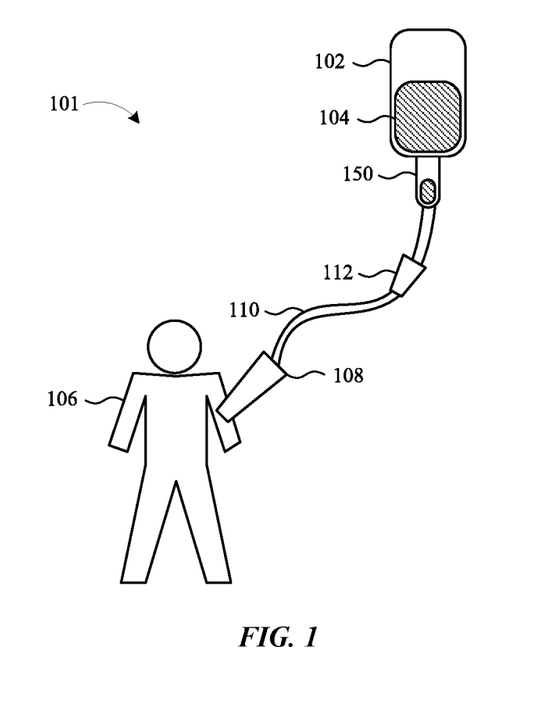
FIG. 1 is a schematic diagram of an example of an IV therapy system.

FIG. 1 is a schematic diagram of an example IV therapy system 101 that can be used to administer fluids to a patient. The IV therapy system 101 includes an IV bag 102 containing a reservoir of fluid 104 to be administered to a patient 106, a catheter 108 inserted into the patient's vein for delivering the IV fluid, and an IV line 110 that provides tubing to convey the fluid from the IV bag 102 to the catheter 108. A drip chamber 150 is coupled between the IV bag 102 and the catheter 108 to form drops of the fluid 104 at a known drop factor. The drop formation in the drip chamber 150 can provide a metric to determine a flow rate, for example, by allowing counting or measurement of the number of drops over a period of time. A control mechanism 112, such as a roller clamp coupled to the IV line, can be used to adjust the flow rate as desired based on the flow rate determined from the drip chamber.

Figure 2:
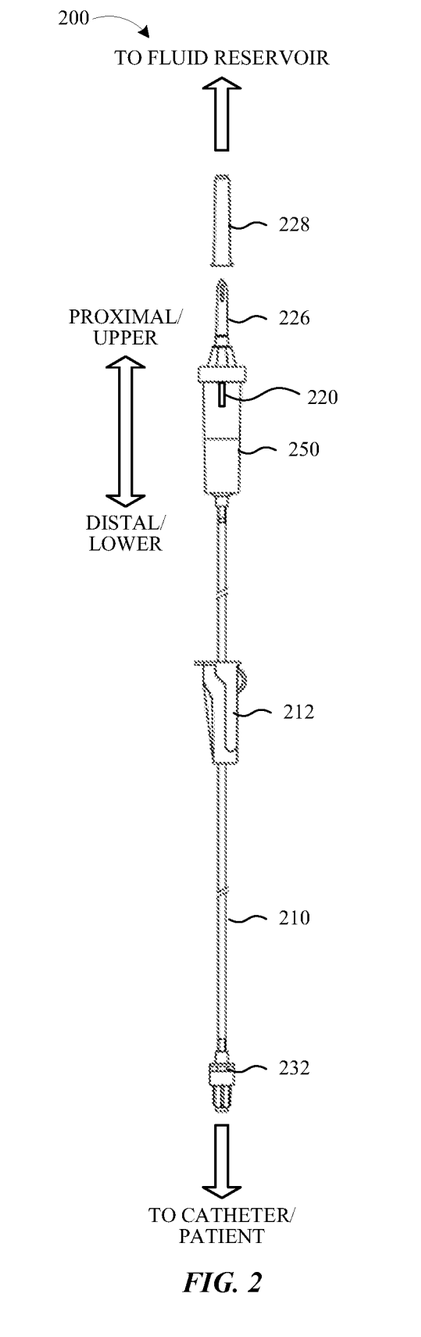
FIG. 2 is a diagram of an example of an infusion set employing a drip chamber.

FIG. 2 is an illustration of an example IV administration set 200. The IV set 200 is a particular example of a device that includes a drip chamber and other operative components of a fluid administration system. The IV set 200 includes a modular design to allow for insertion in and removal from an IV system as desired. The IV set 200 can, for example, be employed in the IV therapy system 101 or any other appropriate fluid administration system.

As shown in FIG. 2, the IV set 200 includes a drip chamber 250, an IV line 210, a luer lock fitting 232, and a roller clamp 212. The drip chamber 250 has a container for holding an IV fluid. A proximal end of the drip chamber 250 can include an inlet port to receive fluid from the fluid reservoir, while a distal end of the drip chamber 250 can include an outlet port to provide the fluid downstream to the patient through an IV line 210. The drip chamber 250 can be configured to receive the fluid using a gravity feed from the fluid reservoir, where the proximal end of drip chamber 250 corresponds to an upper end (or top end) and the distal end corresponds to a lower end (or bottom end) in a gravitational frame of reference. A drop former 220 is suspended from the upper end of the drip chamber 250 and can extend downward from the upper end partially into an interior cavity of the container. The drop former 220 can, for example, be made from plastic, metal, and/or any other suitable material, and the drop former 220 can, for example, include a tube, pin, wire, cylinder, flared tip, or other structure that forms drops of IV fluid that can fall into the container below. During operation, the drip chamber 250 may initially be primed with the IV fluid (e.g., to a level of approximately half full) so that air or other gases are allowed to disperse and do not enter the IV line 210 below upon impact of the drops of the IV fluid, which is a liquid, from the drop former 220.

The IV set 200 includes spike 226 at a proximal end which can contain the inlet port therein and couple to an IV bag (e.g., IV bag 102 of FIG. 1). The IV bag can contain the fluid reservoir, which can provide a source of fluid to be delivered to the patient. The IV set 200 shown in FIG. 2 is implemented with a spike-type drip chamber, with the spike 226 included in a cap at the upper end of the drip chamber 250 so that the drip chamber itself can attach directly to a bottom of the IV bag through the spike 226. A protective cover 228, which is shown removed from the spike 226 in FIG. 2, can cover the spike 226 during initial delivery or transport before use. At the opposing, distal end of the IV set 200 is a male luer fitting 232, which is disposed at the end of a segment of the IV line 210. The male luer fitting 232 provides a connector to couple to downstream or distal components, such as a catheter or an additional IV line segment through which the fluid is delivered to the patient.

A roller clamp 212 is included in the IV set 200 along the IV line. The roller clamp 212 provides a control mechanism allowing for manual adjustment of the flow rate by a user (e.g., a clinician). The drip chamber 250 can include a sufficiently transparent exterior surface to allow the user to see the drops falling from the drop former 220, so that the drip rate of the drops can provide a visual check for the user to determine flow rate. For example, the user may use a stopwatch, count the number of drops over a set period of time, and determine the flow rate based on counted number of drops, the time period, and a known drop factor of the drip chamber 250. Additionally or alternatively, the drip chamber 250 can include a sensor, such as a piezo electric sensor, to count or otherwise detect drops falling in the drip chamber. The user may then adjust the flow rate up or down accordingly by manipulating the roller clamp 212 based on the desired treatment of the patient.

Figure 3:
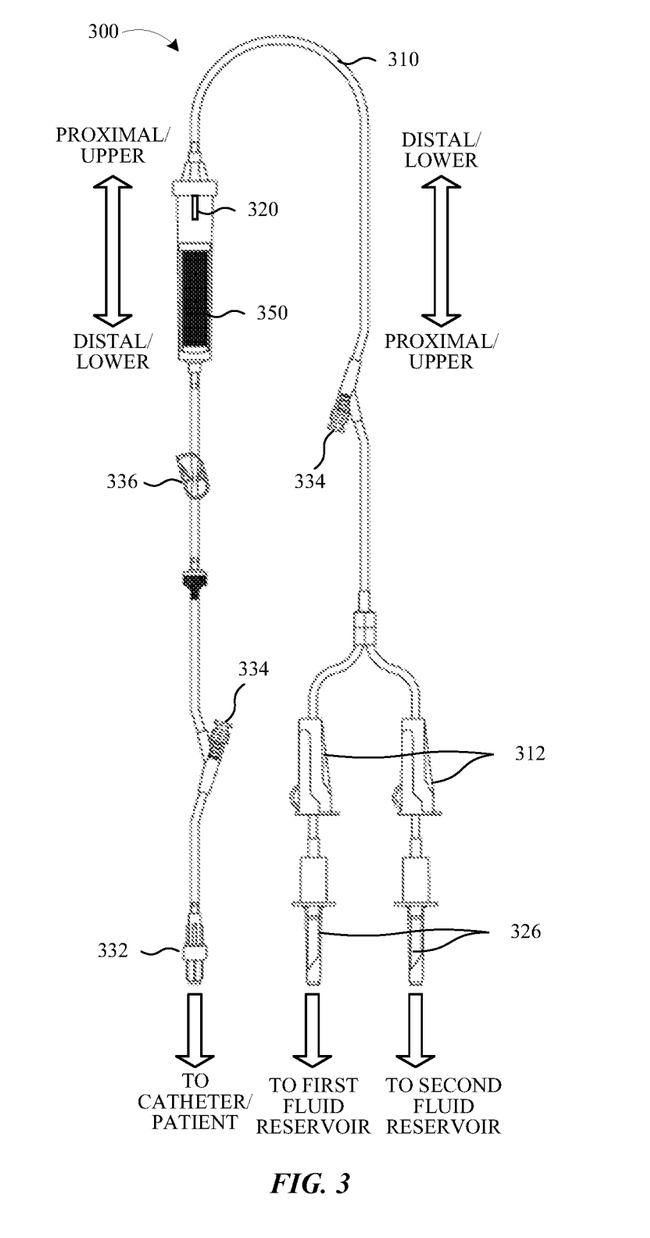
FIG. 3 is a diagram of an example of an infusion set employing an inline drip chamber.

FIG. 3 is an illustration of an example IV set 300. The IV set 300 is another example of a device that includes a drip chamber and other operative components of a fluid administration system. The IV set 300 includes an inline drip chamber 350, which is disposed along an IV line rather than being configured to couple directly to an IV bag like the drip chamber 250 of FIG. 2. The IV set 300 can, for example, be employed in the IV therapy system 101 or any other appropriate fluid administration system.

The top end or cap of the inline drip chamber 350 can include an inlet port coupled to a proximal or upstream segment of the IV line 310 between the drip chamber 350 and the IV bag. The IV set 300 shown in FIG. 3 further includes a pair of connectors at its proximal end for coupling to a pair of respective fluid reservoirs (e.g., an IV bag for saline and a separate IV bag for blood, or any other appropriate combination of fluids to be delivered to a patient). Unlike the example of FIG. 2, in which spike is included directly on the top side or cap of the drip chamber 250 (FIG. 2), the IV set 300 in FIG. 3 includes a pair of spikes 326 respectively disposed at the ends of a pair of IV line segments at the proximal end of the IV set 300.

A pair of roller clamps 312 are provided on the pair of IV line segments, respectively, and can allow for individual adjustment of the flow rate for each respective fluid reservoir. The roller clamps 312 are provided proximal to and upstream from the drip chamber 350, between the drip chamber 350 and fluid reservoirs, in contrast to the IV set 200 of FIG. 2, in which roller clamp 212 (FIG. 2) is disposed distal to and downstream from the drip chamber 250 (FIG. 2), between the drip chamber and the patient. The IV set 300 also includes various additional components to provide additional functionalities. For example, access connectors 334 are shown disposed along the IV line 310 to allow additional fluid transfer devices (e.g., needless syringes or other components) to be coupled to and removed from the IV line 310 for delivery to or removal of additional fluids from the patient as desired. A slider clamp 336 is also shown disposed along the IV line 310 to provide an additional control mechanism for stopping or starting the flow rate.

Figure 4:
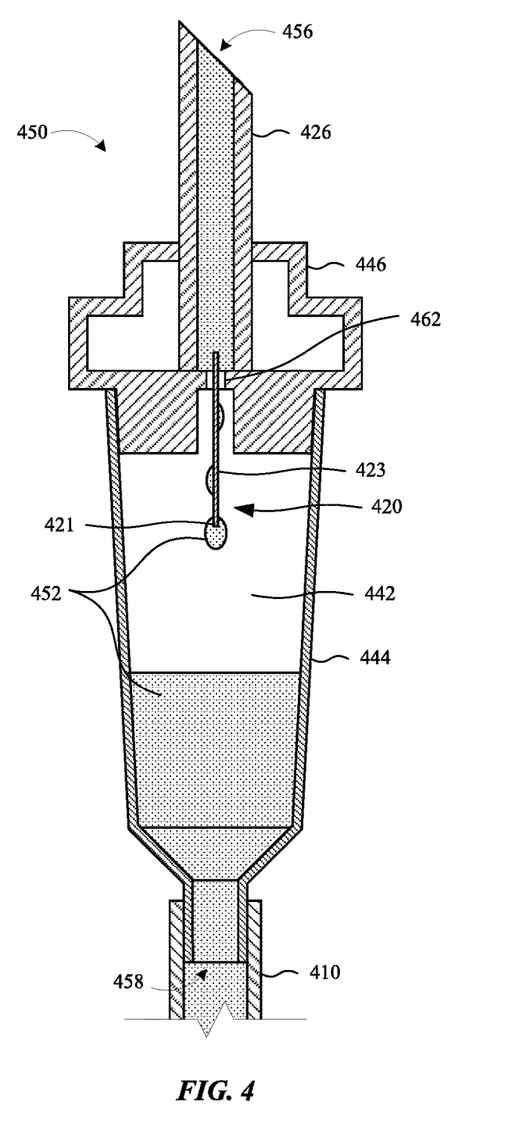
FIG. 4 is a cross section view of an example of a drip chamber employing a lower end that terminates in a solid point.

FIG. 4 is a cross section view of an example drip chamber 450. The drip chamber 450 is a particular example of a drip chamber that employs a solid pin, wire, or other drop former structure providing an outer surface for the IV fluid to descend. The drop former structure can terminate in a small point to encourage the drop, or series of drops, to fall down the outside surface and release from the tip of the drop former at a smaller volume. In some embodiments, the drip chamber 450 can share features in common with any one or more of the drip chambers shown in FIGS. 1-3.

The drip chamber 450 includes a container 444, a cap 446, and an internal cavity 442 within the container and enclosed by the cap 446. The container 444 can have a substantially cylindrical body, or any other appropriate structure to permit holding the IV fluid with an interior cavity of the container body. The cap 446 is disposed on an upper side or proximal end of the container 444, and includes a spike 426, which can be configured to couple to an IV bag containing a fluid (e.g., by insertion of the spike into a bottom end or port in the IV bag). An inlet port 456 is included in the proximal end of the container and can be configured to receive the fluid from the IV bag. As shown in FIG. 4, the inlet port 456 extends through the spike 426 and through the cap 446, and is coupled to a drop former 420 at an upper side or proximal end of the drop former. The inlet port 456 is disposed above the drop former to permit the IV fluid to descend to the drop former. Although shown as including a lumen extending through the cap, in various configurations the inlet port can have any suitable opening, channel, or other structure to permit receipt of IV fluid flowing into the drip chamber. Further, although the drip chamber 450 is shown as including a spike 426 that can be used for direct connection to an IV bag, the drip chamber 450 can additionally or alternatively be implemented as an inline drip chamber that does not employ spike 426, but rather, for example, has an inlet port configured to couple to an upstream segment of an IV line.

The drop former 420 is suspended from the cap 446 and extends distally from the cap 446 in a downward direction partially into the interior cavity 442. The drop former 420 is configured to form a drop of the fluid received from the inlet port 456, and can be configured to release a steady rate of drops into the interior cavity 442 and into the container 444 to permit a flow rate measurement or estimation by counting of the drops. The drop former 420 can, for example, be implemented as a solid pin, wire, or other elongated member. The drop former 420 can terminate in a lower tip 421 (or "distal tip") at its lower or distal end, which provides a release point for a drop of the IV fluid 452 to fall into the container 444.

An outer surface 423 that is between a proximal end and the distal end of the drop former 420 can be coupled directly or indirectly to the inlet port 456 to receive the IV fluid 456 from the inlet port 456. The outer surface 423 can extend in a downward direction and terminate at the distal tip 421 to permit the IV fluid 452 to descend down the outer surface 423 towards a small release point at the distal tip 421. A lateral surface on an exterior of a pin, wire, or other elongated member can provide the outer surface 423 for fluid to descend down. A small solid point at the lower tip 421 below the outer surface 423 can allow formation and release of small drops that may be smaller than those formed by a 60 drop/mL or purely tube type drip chamber having an internal resistance that constrains the size of drops. By way of example, the drop former 420 can be configured (e.g., based on its dimensions) to form drops on the order of 200 to 300 drops/mL, or any other desired size.

The drop former 420 can have a uniform diameter throughout its entire length. Alternatively, the drop former 420 can reduce to a smaller diameter at the distal tip, such as a pin implementation where the distal (lower) tip of the pin has a smaller diameter or size than a proximal (upper) part of the pin. The drop former 420 can have a solid construction throughout its length, with no lumen or interior fluid pathway provided through the entire extent of the drop former, or the drop former 420 can have a solid construction at only a distal section terminating in the distal tip 421, for example, which provides a release point for the drops of the fluid 452.

The drop former 420 can be coupled to the fluid source and coupled to the inlet port 456 through a small hole 462, or pinhole, which can be included in the cap 462 between the upper end of the inlet port 456 and the lower end of the drop former 420. The size of the hole can be sufficiently small so that a surface tension of the fluid prevents a gravity force from allowing a free fall of the fluid through the hole 462. In this example, the drop former 420 includes a proximal section disposed in the hole 462, which can allow the drop former 420 to wick fluid through the hole 462 by capillary action, for example, with a wire shape that wicks fluid similar to the wick of a candle. Alternatively, the drop former 420 may be coupled to the inlet port 456 through any other appropriate structure or arrangement that allows the fluid to descend down the outer surface 423 of the drop former 420.

An outlet port 458 is included at a distal end of the container 444. The outlet port 458 is configured to couple to IV line 410 to allow fluid to be provided downstream from the interior cavity 442 of the drip chamber 450 through the IV line 410 and to the patient. In FIG. 4, the drip chamber 450 is shown after priming with IV fluid 452 to a level at approximately halfway up the container. All or a portion of the container can be made sufficiently transparent to allow the drops falling from the drop former 420 to be visible from an exterior of the drip chamber 450. For example, the container 444 can be made of a transparent plastic, in whole or in part, to allow the formation and/or release of the drops to be visible to a user (e.g., a clinician) from an exterior of the drip chamber 450 to permit manual counting of the drops by the user.

Figure 5:
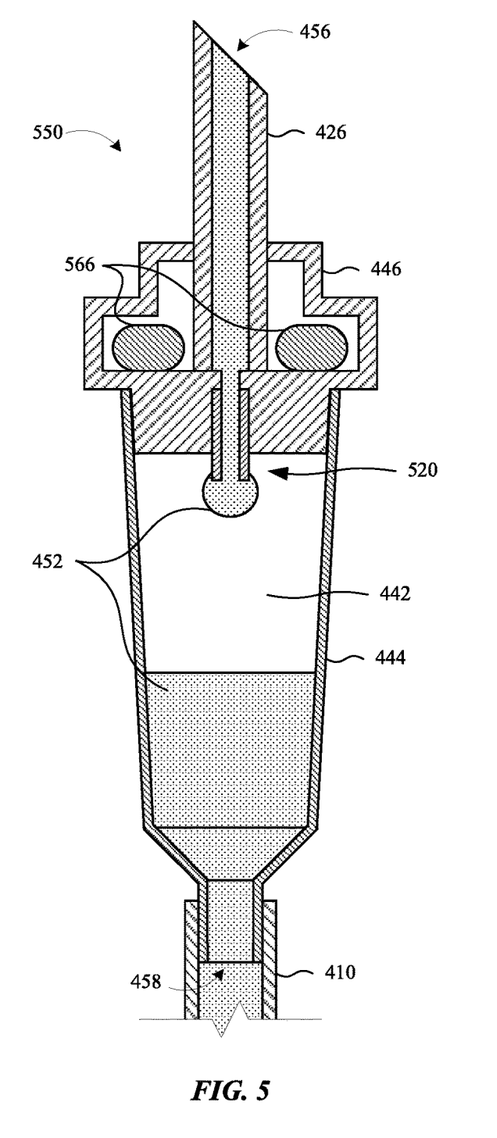
FIG. 5 is a cross section view of an example of a drip chamber employing electronics.

FIG. 5 is a cross section view of an example drip chamber 550. The drip chamber 550 is a particular example of a drip chamber that employs electronics, such as an acoustic emitter, to energize a drop former to stimulate ejection or release of small drops form the drop former. In some embodiments, the drip chamber 550 can share features in common with any one or more of the drip chambers shown in FIGS. 1-4.

The drip chamber 550 includes a drop former 520, which can be suspended from a cap 446 and configured to release a drop of IV fluid 452 into an interior cavity 442 of a container 444. The drop former 520 is shown in FIG. 5 as including a tubular structure having an inner lumen through which the fluid from the inlet port 456 passes through to a distal tip of the tubular structure. Additionally or alternatively, the drop former 520 can employ any suitable structure for forming and releasing drops, such as, for example, a pin or wire with a solid distal tip like that shown in FIG. 4.

The drip chamber 550 includes an electronic component 566 housed within the cap 446. The electronic component 566 is operatively coupled to the drop former 520 and configured to stimulate drop formation and/or release therefrom. The electronic component 566 may be operatively coupled to the drop former directly or through intervening components, such as through the cap, so long as the coupling is sufficient to permit the electronic component to interact with the drop former 520. The electronic component 566 can, for example, include an acoustic emitter, which can be operatively coupled to the drop former 520 through any appropriate physical or mechanical coupling that permits sound waves or other signals emitted from the component 566 to reach a surface of the drop former 520. Additionally or alternatively, the electronic component can include circuitry, a power source (e.g., a battery), wires, and/or other electronics to facilitate energizing the drop former 520.

Acoustic energy or mechanical vibrations generated or otherwise provided by the electronic component 566 can be configured to overcome a resistance or surface tension of the fluid in the drop former to trigger release of a drop that might not otherwise fall relying on gravity or pressure differences alone. The electronic component 566 can, for example, be configured to stimulate the drop former 520 periodically, such as by generating a burst of acoustic energy periodically in synchronization with a predetermined drop rate, which can be fixed or user-programmable.

The electronic component 566 can be housed within an enclosure of the cap 446 that is sealed or otherwise insulated from the fluidic pathway of the fluid 452 (e.g., insulated from the inlet port 456 and the interior cavity 442). This can permit the electronic component 566 to be insulated from sterile components and/or allow the electronic component 566 to be removed from the cap 446 and reused in other drip chambers, while a remaining structure of the drip chamber 550, such as container 544 and/or drop former 520, can be discarded after each instance of use. The electronic component 566 is shown in FIG. 5 as an annular structure at least partially surrounding the inlet fluid pathway, but the electronic component 566 can additionally or alternatively be implemented as one or more discrete structures having any other suitable size or shape.

Figure 6:
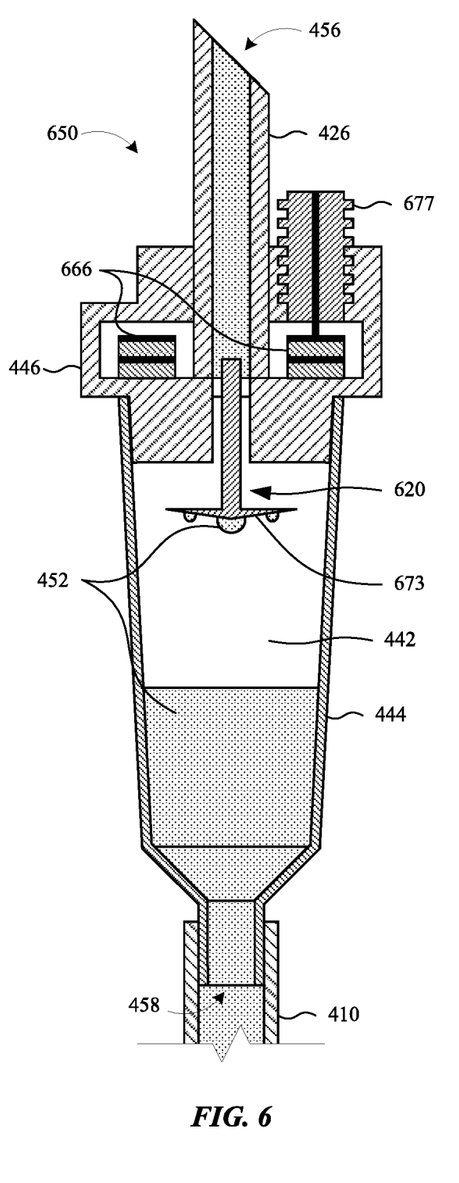
FIG. 6 is a cross section view of an example of a drip chamber employing an ultrasonic emitter.
Figure 7A:
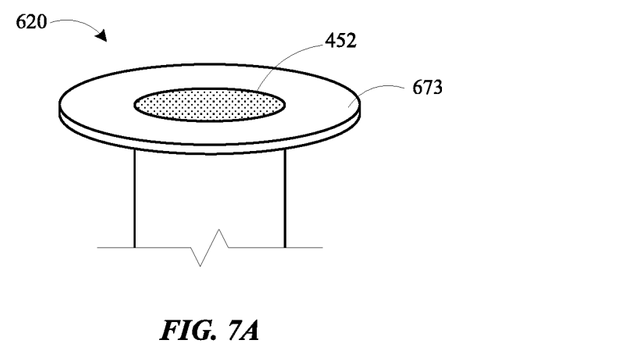
FIGS. 7A-7C are diagrams illustrating an example of a sequence of energizing a drop former with ultrasonic energy.
Figure 7B:
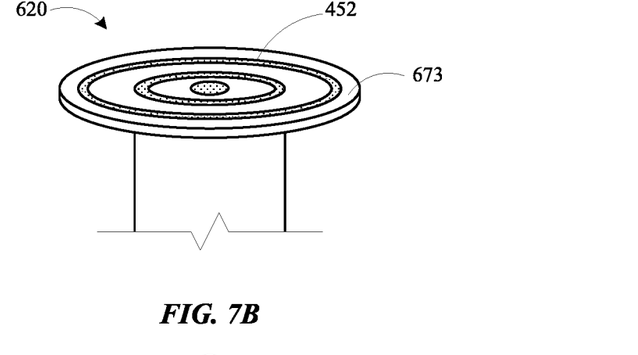
Figure 7C:
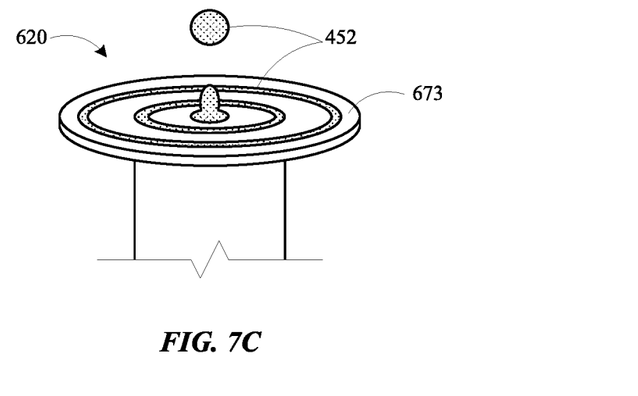

FIG. 6 is a cross section view of an example drip chamber 650. FIGS. 7A-7C are illustrations of a sequence of operating a drop former 620 included in the drip chamber 650. The drip chamber 650 is a particular example of a drip chamber that employs ultrasonic energy to energize a drop former to stimulate ejection or release of small drops from the drop former. In some embodiments, the drip chamber 650 can share features in common with any one or more of the drip chambers shown in FIGS. 1-5.

The drip chamber 650 includes an electronic component housed within the cap 446. In particular, the electronic component is implemented as or otherwise includes an ultrasonic emitter 666 operatively coupled to a drop former 620 that is suspended from a cap 446. The ultrasonic emitter 666 can, for example, include a piezoelectric, capacitive, or other suitable transducer capable of emitting ultrasonic waves to a surface of the drop former 620. The drop former 620 includes a transverse outer surface 673 at a distal or lower tip of the drop former. The transverse outer surface 673 extends substantially orthogonal to the downward direction, or more generally extends transverse to the direction in which drops are released from the drop former 620. This allows the drops to be released from the drop former 620 in a direction generally normal to the outer surface 673. The transverse outer surface 673 may be provided using a flared structure, as shown in FIG. 6, in which the distal, lower end of the drop former is flared radially outward to provide an increased diameter at its lower end. Alternatively, the drop former 620 may be implemented with a solid cylindrical structure (such as a large gauge wire) in which a distal, lower tip provides a transverse surface with sufficient surface area for the ultrasonic emitter to create drops in the manner described herein.

FIG. 6 also shows an external coupling connector 677 which can, for example, permit coupling of the ultrasonic emitter 666 to external electronic components, such as an external power source and/or external ultrasonic generator configured to provide an oscillating signal to the ultrasonic emitter 666 housed within the drip chamber 650. Although the drip chamber 650 is shown as included both an internal ultrasonic emitter 666 and external coupling connector 677, in alternate embodiments only one or the other may be used. For example, in some embodiments, all electronics used for emitting waves to the drop former 620 can be housed entirely within the cap 446. Alternatively, all the electronics including the ultrasonic emitter 666 can be provided externally and coupled to the drop former through one or more external coupling connectors.

The ultrasonic emitter 666 can be configured to generate standing waves of an IV fluid 452 at the surface of the drop former 620 to allow creating of very small drops or droplets that can have a smaller diameter than the transverse surface 673. FIGS. 7A-7C illustrate an example sequence of drop creation at drop former 620 using ultrasonic electronics to energize the drop former and create standing waves at the transverse surface 673. In FIGS. 7A-7C, the drop former 620 is shown in inverted form to better show the surface 673 and wave generation.

FIG. 7A shows the drop former 620 with IV fluid resting on the surface 673 when no ultrasonic waves or energy are provided to the surface. In this state, the fluid can form a relatively large clump. In FIG. 7B, ultrasonic waves are coupled to the surface 673 to cause the formation of standing waves which generally cause the clump of IV fluid 452 to separate into smaller sections or smaller peaks and valleys. In this state, the IV fluid 452 has not yet released from the drop former. In FIG. 7C, the waves have crested after their amplitudes have increased sufficiently to cause release of one or more small drops or droplets of the IV fluid 452, which can generally have a diameter smaller than a diameter of the transverse surface 673 at the tip of the drop former 620. Although the waves are shown with a generally circular or annular pattern in FIGS. 7A-7C, in various implementations the waves and/or drops released from the ultrasonic drop former 620 may generally have any appropriate size, shape, or pattern, as desired. For example, the use of ultrasonic electronics may also allow the size, pattern, or rate of drop creation to be fine-tuned by adjusting the waveform (e.g., by adjusting shape, frequency, and/or amplitude of the ultrasonic waves) provided to the transverse outer surface 673.

Figure 8:
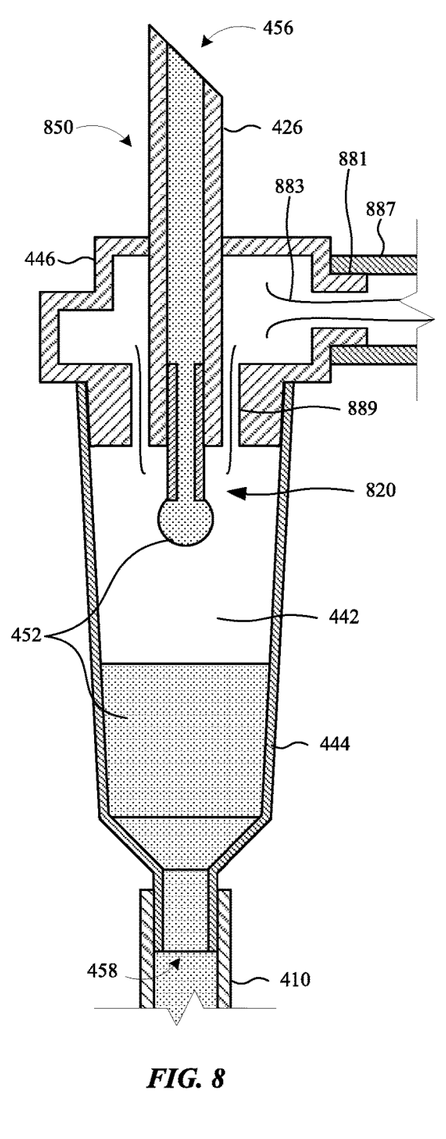
FIG. 8 is a cross section view of an example of a drip chamber employing injected air.

FIG. 8 is a cross section view of an example drip chamber 850. The drip chamber 850 is a particular example of a drip chamber that employs injected air to stimulate a release of a drop from the drop former. In some embodiments, the drip chamber 850 can share features in common with any one or more of the drip chambers shown in FIGS. 1-7.

The drip chamber 850 includes a gas inlet port 881 coupled to a drop former 820 via a fluidic pathway to permit an injected gas 883 (e.g., sterile air or another gas) to stimulate a release of a small drop from the drop former 820, which can receive an IV fluid from liquid inlet port 456. A gas injection component 887 can be coupled to the gas inlet port 881 to inject a gas into an interior of the drip chamber, where it can stimulate a surface of the drop former to trigger a release of a drop of IV fluid 452. The gas injection component 887 can include, for example, a compressed gas cartridge, or a tubing segment coupled to a pressurized gas tank, a pump, or other source of gas in a facility (e.g., a hospital).

The gas inlet port 881 can be operatively coupled to the drop former via a fluidic pathway that permits the injected gas 883 to reach the drop former. For example, a gas orifice 889 can be provided in the cap immediately above the drop former to permit gas 883 injected through the gas inlet port 881 to reach the drop former 820. Alternatively, other structures may be used to permit the gas inlet port 881 to be operatively coupled to the drop former to stimulate release of drops therefrom. In some embodiments, the injected gas may be delivered in a series of bursts timed in synchronization with a predetermined drip rate, which may be fixed or user-programmable. For example, a small disposable compressed gas cartridge may be provided with the drip chamber 850 and configured to meter out the injected gas through the gas inlet port in a series of small bursts. This may allow for the desired drip rate while also permitting compressed gas contained within the compressed gas cartridge to last for a duration of use of the drip chamber 850.

Figure 9:
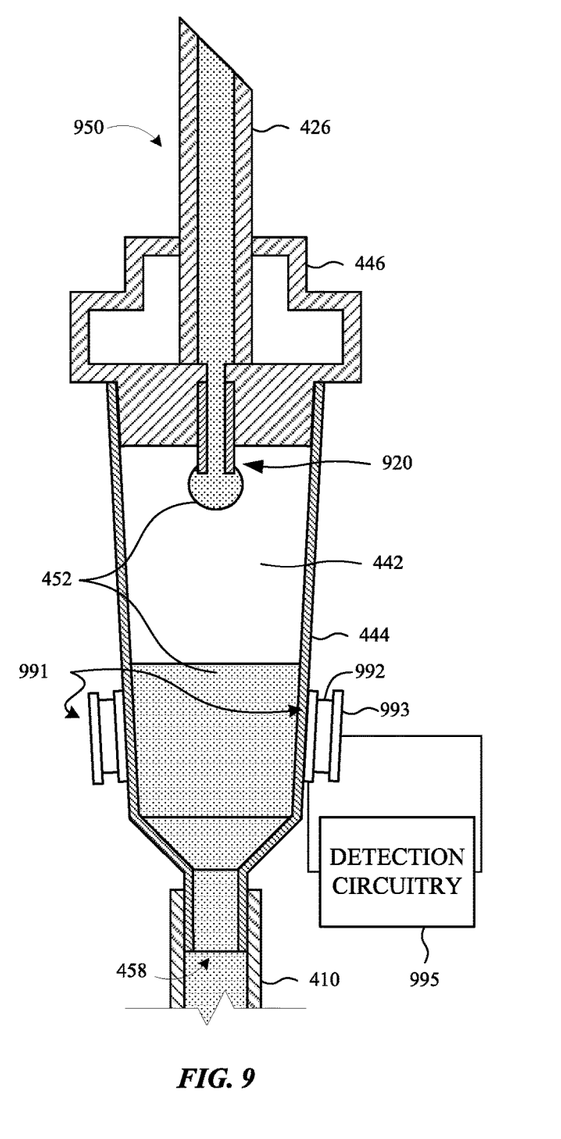
FIG. 9 is a cross section view of an example of a drip chamber employing a piezo electric sensor.

FIG. 9 is a cross section view of an example drip chamber 950. The drip chamber 950 is a particular example of a drip chamber that employs a piezoelectric sensor to detect drip rate of drops falling within the drip chamber, which may, for example, permit drops to be counted at a rate faster than the human eye can reliably see. In some embodiments, the drip chamber 950 can share features in common with any one or more of the drip chambers shown in FIGS. 1-8.

The drip chamber 950 includes a piezo electric sensor 991 coupled to a container 444 to detect drops falling within the container. The piezo electric sensor 991 can, for example, include a passive piezo electric material 992 that acts as a microphone to detect the impact of drops of the IV fluid 452 falling into the container 444 from the drop former 920. In the example shown in FIG. 9, the piezo electric sensor 991 includes one or more electrodes 993 coupled to the piezoelectric material 992. The piezoelectric material 992 can, for example, be a passive piezo electric material. The electrode(s) 993 can be coupled to detection circuitry 995 which is configured to measure a signal and/or determine a flow rate by counting a number of drops falling into the container 444. The detection circuitry 995 can generally include any one or more analog and/or digital circuits, processor(s), microcontroller(s), and/or other circuitry suitable for processing a signal received from the piezoelectric sensor 992. The detection circuitry 995 can, for example, be contained within the same physical module or sensor package as the piezo electric sensor 991, or may be physically separate communicatively coupled to the piezo electric sensor 991 through one or more wired and/or wireless interconnections.

The piezo electric sensor 991 can be disposed outside of the container 444 and outside of the interior cavity 442 to insulate the piezo electric sensor 991 from physical contact with the IV fluid 452 delivered to the patient. The piezoelectric sensor 991 can be attached to a sidewall of the container 444 to facilitate pickup of the signal from drop impact within the cavity 442 by the sensor 991. The piezoelectric sensor 991 can also be disposed below a fluid level where the IV fluid is initially primed, for example, below a midway point of the container body. This may also facilitate pickup of the signal of each drop upon impact to be picked up by the sensor, as the IV fluid 452 can act as a transmission medium for the acoustic or mechanical impact of falling drops.

Figure 10:
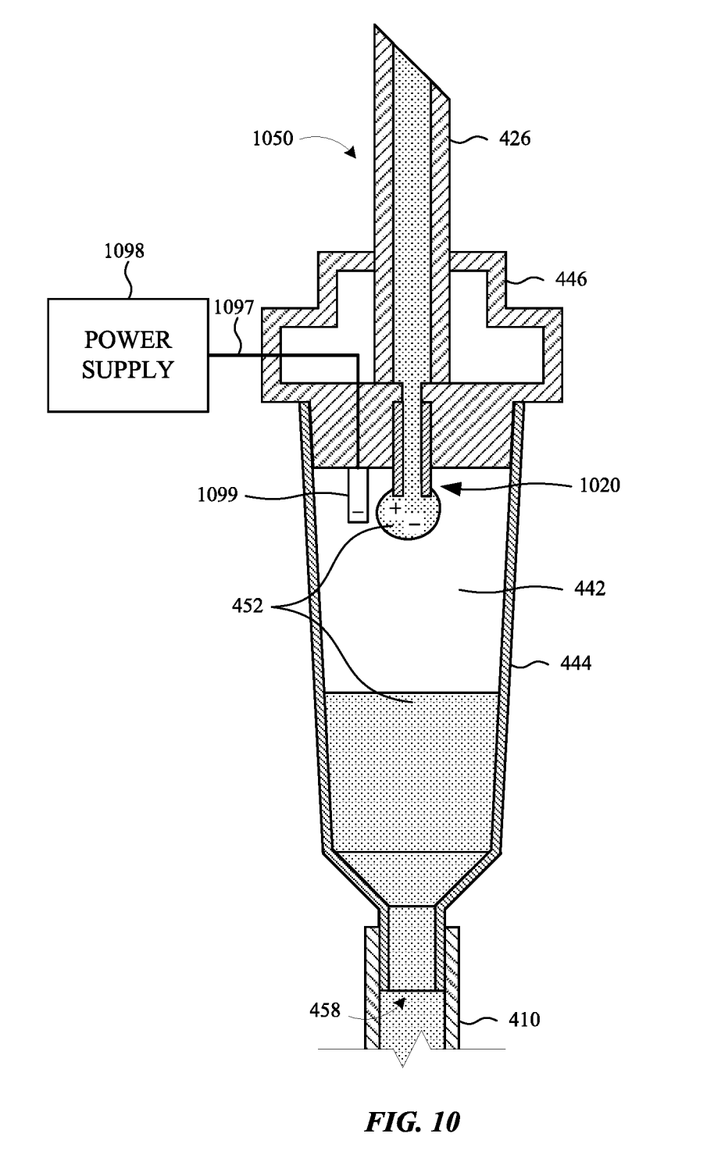
FIG. 10 is a cross section view of an example of a drip chamber employing a charged electrode.

FIG. 10 is a cross section view of an example drip chamber 1050. The drip chamber 1050 is a particular example of a drip chamber that employs a charged electrode to attract polar molecules (e.g., water molecules) in the IV fluid 452 and dislodge drops of the IV fluid 452 at a volume smaller than may be possible with gravity alone. In some embodiments, the drip chamber 1050 can share features in common with any one or more of the drip chambers shown in FIGS. 1-9.

The drip chamber 1050 includes an electrode 1099, which is disposed sufficiently close to the drop former 1020 to attract a polar molecule in the IV fluid 452 based on a charge applied to or otherwise held in the electrode 1099. For example, as shown in FIG. 10 the electrode 1099 can be negatively charged, which can attract a positive end of water molecules within the drop former to effect a release of drops. As another example, in some embodiments the electrode 1099 can be positively charged to attract a negative end of water molecules or other polar molecules in the IV fluid 452. In the example shown in FIG. 10, the electrode 1099 is disposed within the interior cavity 442 of the container 444 and suspended from the cap 446 in a region near the tip of the drop former 1020. However, implementations are contemplated in which the electrode 1099 can be disposed in any other suitable location to permit the electrode to attract polar molecules in the IV fluid 452. For example, in some embodiments the electrode 1099 can be implemented as all or a portion of the container 444 itself. The drop former 1020 is shown as having a tubular structure in FIG. 10 but can in various embodiments employ any suitable structure for forming and releasing drops, such as, for example, a pin or wire with a solid distal tip like that shown in FIG. 4.

In the example shown in FIG. 10, the electrode 1099 is coupled to a wire 1097 to connect the electrode 1099 to a power supply 1098 that applies a charge to the electrode (e.g., by applying a voltage to the electrode 1099). The power supply 1098 can be disposed externally to the container 444 and cap 446, such as, for example, as part of a pump system used for pumping fluid through an IV system, or any other appropriate electronic system in a facility. Alternatively, the power supply 1098 can be, for example, a battery housed within the cap 446. In either case, the wire 1097 coupled to the electrode 1099 can, for example, extend at least partially through the cap to provide a signal path for charging the electrode 1099.

Various examples of aspects of the disclosure are described below as clauses for convenience. These are provided as examples, and do not limit the subject technology. As an example, some of the clauses described below are illustrated in FIGS. 1-10.

Clause 1. A drip chamber comprising:
a container configured to hold an intravenous (IV) fluid;
a drop former suspended over the container, the drop former having an upper end, a lower tip, and an outer surface extending between the upper end and the lower tip; and
an inlet port disposed above the drop former and configured to receive the IV fluid from a reservoir,
wherein the inlet port is coupled to the outer surface to permit the IV fluid to descend down the outer surface.

Clause 2. The drip chamber of Clause 1 or any other Clause herein, further comprising:
a cap disposed on an upper side of the container,
wherein the drop former is suspended from the cap,
wherein the drop former includes a solid pin or wire elongated in a downward direction,
wherein a lateral surface on an exterior of the solid pin or wire provides the outer surface, and
wherein an outlet port is disposed at a lower end of the container, the outlet port being configured to couple to an IV line to deliver the IV fluid to a patient.

Clause 3. The drip chamber of Clause 1 or any other Clause herein, wherein the drop former includes a solid pin.

Clause 4. The drip chamber of Clause 1 or any other Clause herein, wherein the drop former includes a wire.

Clause 5. The drip chamber of Clause 1 or any other Clause herein, wherein the drop former extends in a downward direction and terminates in a solid point at the lower tip.

Clause 6. The drip chamber of Clause 1 or any other Clause herein, further comprising:
a cap disposed on an upper side of the container, wherein the inlet port is disposed in the cap and the drop former is suspended from the cap; and
a hole disposed in the cap below the inlet port, wherein the outer surface of the drop former is coupled to the inlet port through the hole to wick the IV fluid through the hole.

Clause 7. The drip chamber of Clause 1 or any other Clause herein, further comprising:
a piezoelectric sensor coupled to the container to detect a drop falling into the container from the drop former.

Clause 8. The drip chamber of Clause 1 or any other Clause herein, further comprising:
an electrode disposed sufficiently close to the drop former to attract a polar molecule in the IV fluid based on a charge held in the electrode.

Clause 9. A drip chamber comprising:
a container configured to hold an IV fluid;
a drop former suspended over the container and coupled to an inlet port to receive the IV fluid from a reservoir; and an acoustic emitter operatively coupled to the drop former to stimulate a release of a drop of the IV fluid from the drop former.

Clause 10. The drip chamber of Clause 9 or any other Clause herein, further comprising:
a cap disposed on an upper side of the container,
wherein the drop former is suspended from the cap,
wherein the acoustic emitter is an ultrasonic emitter housed within the cap, and
wherein an outlet port is disposed at a lower end of the container, the outlet port being configured to couple to an IV line to deliver the IV fluid to a patient.

Clause 11. The drip chamber of Clause 9 or any other Clause herein, wherein the acoustic emitter is an ultrasonic emitter configured to create standing waves of the IV fluid at a surface of the drop former.

Clause 12. The drip chamber of Clause 9 or any other Clause herein, further comprising:
a cap disposed on an upper side of the container,
wherein the drop former is suspended from the cap, and
wherein the acoustic emitter is housed within the cap.

Clause 13. The drip chamber of Clause 9 or any other Clause herein, wherein a lower tip of the drop former is flared outward.

Clause 14. The drip chamber of Clause 9 or any other Clause herein, wherein the drop former has a solid cylindrical structure.

Clause 14. The drip chamber of Clause 9 or any other Clause herein, wherein the drop former is elongated in a downward direction and has a transverse outer surface extending transverse to the downward direction, wherein the acoustic emitter is an ultrasonic emitter configured to create the drop with a diameter smaller than a diameter of the transverse outer surface.

Clause 16. A drip chamber comprising:
a container configured to hold an IV fluid;
a drop former suspended over the container and coupled to an inlet port to receive the IV fluid from a reservoir; and
a piezoelectric sensor coupled to the container to detect a drop falling into the container from the drop former.

Clause 17. The drip chamber of Clause 16 or any other Clause herein, further comprising:
a cap disposed on an upper side of the container,
wherein the drop former is suspended from the cap,
wherein an outlet port is disposed at a lower end of the container, the outlet port being configured to couple to an IV line to deliver the IV fluid to a patient, and
wherein the piezoelectric sensor is attached to a sidewall of the container below a midway point of the container.

Clause 18. The drip chamber of Clause 16 or any other Clause herein, wherein the piezoelectric sensor is disposed outside the container below a fluid level of the container.

Clause 19. The drip chamber of Clause 16 or any other Clause herein, further comprising:
detection circuitry coupled to the to the piezoelectric sensor and configured to determine a flow rate by counting a number of drops falling into the container.

Clause 20. The drip chamber of Clause 16 or any other Clause herein, wherein the piezoelectric sensor comprises a piezoelectric material and an electrode coupled to the piezoelectric material.

Clause 21. The drip chamber of Clause 16 or any other Clause herein, wherein the drop former comprises at least one of a tube, a pin, a wire, a cylinder, and a flared tip.

Clause 22. A drip chamber comprising:
a container configured to hold an IV fluid;
a drop former suspended over the container and coupled to a liquid inlet port to receive the IV fluid from a reservoir; and
a gas inlet port coupled to the drop former via a fluidic pathway to permit an injected gas to stimulate a release of a drop of the IV fluid from the drop former.

Clause 23. The drip chamber of Clause 22 or any other Clause herein, further comprising:
a cap disposed on an upper side of the container,
wherein the drop former is suspended from the cap,
wherein the gas inlet port is disposed in the cap, and
wherein an outlet port is disposed at a lower end of the container, the outlet port being configured to couple to an IV line to deliver the IV fluid to a patient.

Clause 24. The drip chamber of Clause 22 or any other Clause herein, further comprising:
a tubing segment coupled to the gas inlet port and configured to convey the injected gas from a source to the gas inlet port.

Clause 25. The drip chamber of Clause 22 or any other Clause herein, further comprising:
a compressed gas cartridge coupled to the gas inlet port and configured to inject the injected gas through the gas inlet port.

Clause 26. The drip chamber of Clause 25 or any other Clause herein, wherein the compressed gas cartridge is configured to meter out the injected gas through the gas inlet port in a series of bursts synchronized with a predetermined drip rate.

Clause 27. A drip chamber comprising:
a container configured to hold an IV fluid;
a drop former suspended over the container and coupled to an inlet port to receive the IV fluid from a reservoir; and
an electrode disposed sufficiently close to the drop former to attract a polar molecule in the IV fluid based on a charge held in the electrode.

Clause 28. The drip chamber of Clause 27 or any other Clause herein, further comprising:
a cap disposed on an upper side of the container,
wherein the drop former is suspended from the cap,
wherein the electrode is suspended from the cap and coupled to a wire extending at least partially through the cap to connect the electrode to a power supply, and
wherein an outlet port is disposed at a lower end of the container, the outlet port being configured to couple to an IV line to deliver the IV fluid to a patient.

Clause 29. The drip chamber of Clause 27 or any other Clause herein, wherein the electrode is disposed in the container.

Clause 30. The drip chamber of Clause 27 or any other Clause herein, wherein the electrode is at least part of the container.

Clause 31. The drip chamber of Clause 27 or any other Clause herein, wherein the electrode is negatively charged.

Clause 32. The drip chamber of Clause 27 or any other Clause herein, wherein the electrode is positively charged.

Clause 33. The drip chamber of Clause 27 or any other Clause herein, wherein the electrode is coupled to a power supply configured to apply a charge to the electrode.

Clause 34. The drip chamber of Clause 33 or any other Clause herein, further comprising:
   a cap disposed on an upper side of the container, wherein the power supply is external to the cap and the container.

Clause 35. The drip chamber of Clause 33 or any other Clause herein, further comprising:
   a cap disposed on an upper side of the container, wherein the power supply is a battery housed within the cap.

Clause 36. An IV administration set, comprising:
   a spike configured to couple to an IV bag containing a reservoir of IV fluid;
   an IV line segment disposed distal to the spike, the IV line segment having a distal end terminating in a luer fitting; and
   a drip chamber coupled between the IV line segment and the spike, the drip chamber being configured according to any of the drip chambers recited in Clauses 1 to 35.

Clause 37. An IV therapy system, comprising:
   an IV bag containing a reservoir of IV fluid;
   a catheter configured to deliver the IV fluid to a vein of a patient; and
   a drip chamber coupled between the IV bag and the catheter, the drip chamber being configured according to any of the drip chambers of Clauses 1 to 35.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) or § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A drip chamber comprising:
a container configured to hold an intravenous (IV) fluid;
a drop former suspended over the container, the drop former comprising a longitudinal body uniformly extending from an upper end to a lower tip and having a solid construction with no interior fluid pathway provided between the upper end and lower tip, and an outer surface extending between the upper end and the lower tip;
an inlet port disposed above the drop former and configured to receive the IV fluid from a reservoir, wherein the inlet port is coupled to the outer surface to permit the IV fluid to descend down the outer surface; and
an electrode disposed sufficiently close to the drop former to attract a polar molecule in the IV fluid based on a charge held in the electrode, the electrode configured to stimulate a release of a drop of the IV fluid from the drop former into the container.

2. The drip chamber of claim 1, further comprising:
a cap disposed on an upper side of the container,
wherein the drop former is suspended from the cap,
wherein the drop former includes a solid pin or wire elongated in a downward direction,
wherein a lateral surface on an exterior of the solid pin or wire provides the outer surface, and
wherein an outlet port is disposed at a lower end of the container, the outlet port being configured to couple to an IV line to deliver the IV fluid to a patient.

3. The drip chamber of claim 1, wherein the drop former includes a solid pin.

4. The drip chamber of claim 1, wherein the drop former includes a wire.

5. The drip chamber of claim 1, wherein the drop former extends in a downward direction and terminates in a solid point at the lower tip.

6. The drip chamber of claim 1, further comprising:
a cap disposed on an upper side of the container, wherein the inlet port is disposed in the cap and the drop former is suspended from the cap; and
a hole disposed in the cap below the inlet port, wherein the outer surface of the drop former is coupled to the inlet port through the hole to wick the IV fluid through the hole.

7. The drip chamber of claim 1, further comprising:
a piezoelectric sensor coupled to the container to detect a drop falling into the container from the drop former.

8. A drip chamber comprising:
a container configured to hold an IV fluid;
a cap disposed on an upper side of the container;
a drop former suspended from the cap and extending into the container and coupled to an inlet port to receive the IV fluid from a reservoir, the drop former comprising a longitudinal body uniformly extending from an upper end to a lower tip and having a solid construction with no interior fluid pathway provided between the upper end and lower tip; and
an acoustic emitter housed within the cap and operatively coupled to the drop former to stimulate a release of a drop of the IV fluid from the drop former.

9. The drip chamber of claim 8, further comprising:
an outlet port is disposed at a lower end of the container, the outlet port being configured to couple to an IV line to deliver the IV fluid to a patient.

10. The drip chamber of claim 8, wherein the acoustic emitter is an ultrasonic emitter configured to create standing waves of the IV fluid disposed on a surface of the drop former.

11. The drip chamber of claim 8, wherein a lower tip of the drop former is flared outward.

12. The drip chamber of claim 8, wherein the drop former has a solid cylindrical structure.

13. The drip chamber of claim 8, wherein the drop former is elongated in a downward direction and has a transverse outer surface extending transverse to the downward direction, wherein the acoustic emitter is an ultrasonic emitter configured to create the drop with a diameter smaller than a diameter of the transverse outer surface.

14. The drip chamber of claim 8, further comprising:
a piezoelectric sensor coupled to the container to detect a drop falling into the container from the drop former.

15. The drip chamber of claim 14, further comprising:
an outlet port disposed at a lower end of the container, the outlet port being configured to couple to an IV line to deliver the IV fluid to a patient, and
wherein the piezoelectric sensor is attached to a sidewall of the container below a midway point of the container.

16. The drip chamber of claim 14, wherein the piezoelectric sensor is disposed outside the container below a fluid level of the container.

17. The drip chamber of claim 14, further comprising:
detection circuitry coupled to the to the piezoelectric sensor and configured to determine a flow rate by counting a number of drops falling into the container.

18. The drip chamber of claim 14, wherein the piezoelectric sensor comprises a piezoelectric material and an electrode coupled to the piezoelectric material.

* * * * *